United States Patent [19]

Mangiardi et al.

[11] 4,135,880

[45] Jan. 23, 1979

[54] FOLATE ASSAY WITH ION EXCHANGE RESIN BOUND-FREE SEPARATION

[75] Inventors: Vito J. Mangiardi, San Rafael; Henry J. Jeong, Sacramento; Nathan Lewin, Corte Madera, all of Calif.

[73] Assignee: Bio-Rad Laboratories, Inc., Richmond, Calif.

[21] Appl. No.: 826,006

[22] Filed: Aug. 19, 1977

[51] Int. Cl.$^2$ .................... G01N 33/16; G01N 31/06
[52] U.S. Cl. ................... 23/230 B; 23/230.6; 424/1; 23/915; 23/920
[58] Field of Search .......... 424/1; 23/230.6, DIG. 16, 23/DIG. 21, 230 B

[56] References Cited

U.S. PATENT DOCUMENTS

| | | | |
|---|---|---|---|
| 4,015,939 | 4/1977 | Lewin et al. | 23/230 B |
| 4,028,465 | 6/1977 | Lewin et al. | 424/1 |

*Primary Examiner*—Leland A. Sebastian
*Attorney, Agent, or Firm*—Townsend and Townsend

[57] ABSTRACT

Improved competitive binding serum folate assay in which serum folate bound by folate-selective protein is separated from free serum folate by removal with an anion exchanger, preferably intermediate base anion exchange resin. Preferable are resins characterized by having an aliphatic lattice, particularly, a polyalkyleneamine lattice having tertiary and quaternary amine groups. The resin is advantageously added for the separation function in tablet form.

12 Claims, 1 Drawing Figure

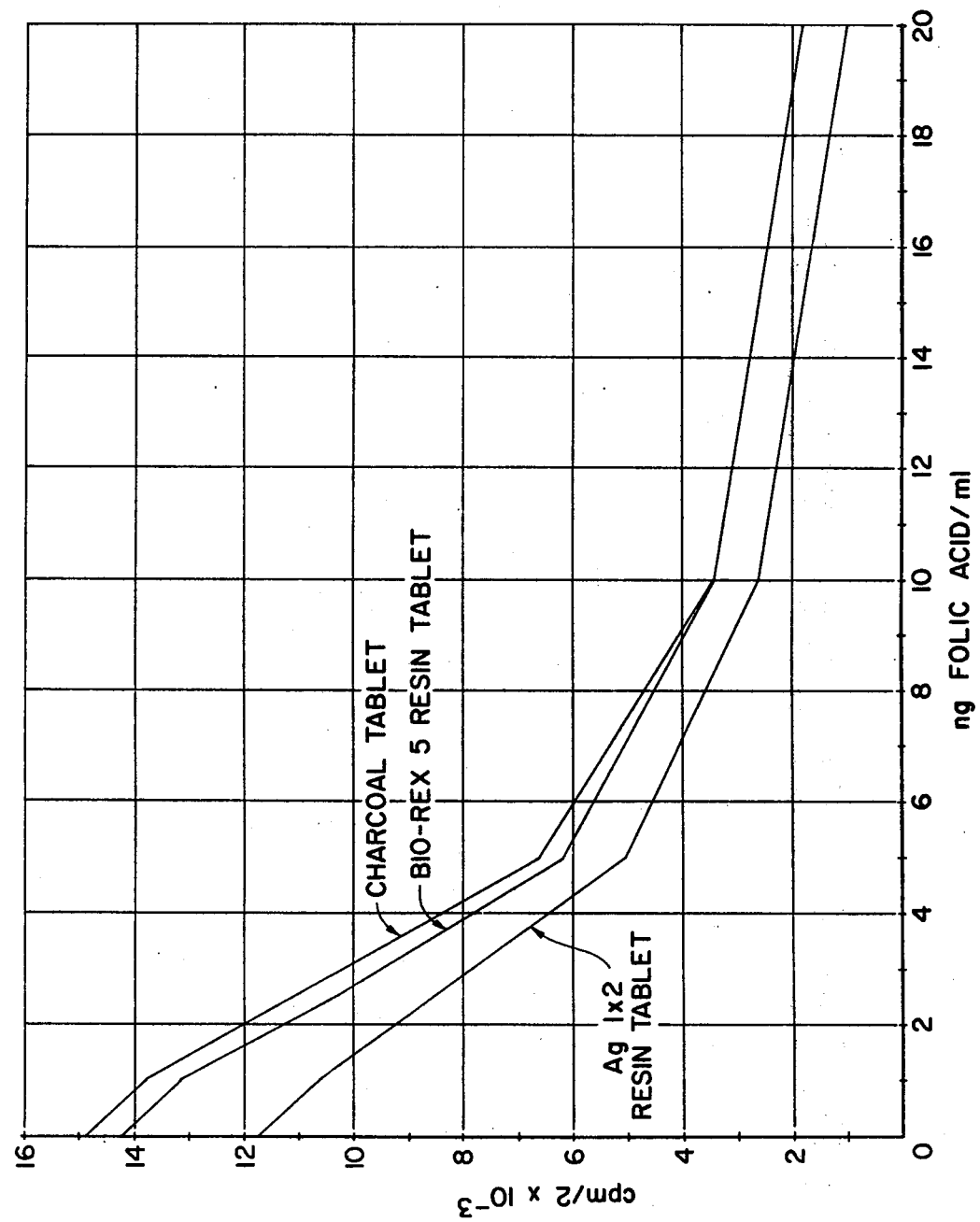

FOLATE ASSAY WITH ION EXCHANGE RESIN BOUND-FREE SEPARATION

This invention relates to an assay procedure for serum folate. More particularly, it relates to the use of anion exchange resin in the "bound-free" separation step during the assay procedure.

U.S. Pat. No. 4,028,465 describes a serum folate assay procedure utilizing the competitive binding technique. The present invention represents an improvement on the process of that patent, the specification thereof being incorporated herein by reference.

In a folate competitive binding assay a measured amount of patient serum is mixed with a folate protecting buffer and a suitable radioactively labelled tracer such as a labelled folate $^{125}$I (pteroylglutamic acid -"PGA") derivative. Under the influence of heat, folate binding proteins are inactivated while the protective agent stabilizes the folate.

The mixture is then incubated with a measured amount of binding protein. An example is the folate selective preparation of $\beta$-lactoglobulin. The amount of the material used is sufficient to bind some, but not all, of the labelled and unlabelled folate present in the mixture. During incubation, the labelled and unlabelled folate compete for the available binding sites of the binding protein on the basis of their concentrations. The more unlabelled folate the sample contains, the less labelled folate will bind to the binding protein. Following incubation the bound folate and unbound or free folate are separated and either phase subjected to quantitation. The degree to which the binding of labelled folate is inhibited by the unlabelled folate present in the serum sample is then determined, and unknown concentration determined from a standard curve.

In practicing the above described type of procedure the above referenced patent utilizes dextran coated charcoal, preferably in a tablet form, for executing the separation of free from competitively bound folate. While the charcoal tablets have to date been successfully utilized including large scale commercial utilization, they have several drawbacks. In particular, charcoal is an undesirably messy material in the clinical laboratory.

In accordance with the present invention the charcoal materials described in the above referenced patent are replaced by an anion exchanger, preferably an intermediate base anion exchange resin. Such a resin eliminates the undesirable aspects of charcoal. Moreover, it has been unexpectedly found that the intermediate base anion exchange resin exhibits lower nonspecific binding relative to the radioactive tracer utilized in the procedure. This advantage increases with time during the recommended shelf life period of the tracer materials. For example and as will be demonstrated more specifically hereinafter, it has been found that there is a decrease of more than about 20% of nonspecific binding with the use of the present intermediate base anion exchange resin as compared with charcoal tablets used in the bound from free separation step.

The intermediate base anion exchange resins utilized in the present invention are described in U.S. Pat. No. 4,015,939. These resins preferably have an aliphatic lattice such as a polyalkyleneamine and have tertiary and quaternary amines thereon. For example, a resin for use in this invention may be described as one having the following structural groupings:

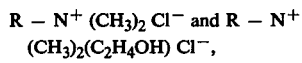

wherein R = polyalkyleneamine lattice.

Preferably of such a material is the resin commercially available from Bio-Rad Laboratories, Inc., of Richmond, California, and sold under the Trademark BIO-REX 5. Other useful intermediate base anion exchange resins are available, including the resin offered by Dow Chemical Company known as Dowex XFS 40396 and the resin available from Ionac Chemical Company known as IONAC-A-305. All of these resins are known as intermediate base anion exchange resins and commonly have an aliphatic lattice. Other lattices such as polystyrene are acceptable.

The term intermediate base anion exchange resin is used in the conventional manner employed in the chromatography art. As is understood, intermediate base resins differ from, for example, strong base resins in that the strong base contains only quaternary groups, whereas intermediate base contains a mixture of tertiary and quaternary amine groups. In general, the intermediate base anion exchange resin contains a mixture of primarily tertiary amine groups with a minor portion of quaternary amine groups. For example, an intermediate base anion exchanger may contain weak base anion exchangers and about 10–20% strong anion groups.

In the preferred embodiment the present intermediate base anion exchange resin is added to the competitive binding solution in tablet form and distributed therein preferably by mixing. The tablets are formulated so that the addition of one tablet to a test solution will introduce about 3–140 mg and preferably about 8–67 mg of resin for each 0.1 ml of serum in the test solution. In the preferred embodiment the intermediate base anion exchange resin is compressed with microcrystalline cellulose, preferbly in a weight ratio of resin to cellulose of about 1:2. The cellulose serves as a bulking and tableting agent and provides a physical form which readily breaks up when added to the competitive binding solution but which maintains physical integrity prior to such use.

In all cases the intermediate base anion exchange resin utilized generally has a wet mesh size of about 50 or higher, preferably 200–400.

A strong anion exchange resin may be used to separate free from bound as demonstrated by the dose response (FIG. 1). Thus type of procedure would also constitute an improvement vis-a-vis the charcoal procedure. However, the reduced "stripping" of bound complex as evidenced by improved trace binding (refer to Table) using the intermediate anion exchanger proves the intermediate exchanger to be best suited for separation of the free-bound folate complex. Superior sensitivity has been demonstrated in the case of intermediate exchanger. This is described in detail in the preferred embodiment.

In general, the present serum folate assay method may be practiced the same as that described in the above referenced 4,5, Pat. No. 4,028,465, including the use of improved stabilizers and tracers described therein if desired, with the only substantial difference being the use of the present anion exchanger, preferably an intermediate base anion exchange resin instead of the charcoal of that patent. The following flow sheet covers a typical assay procedure.

FLOW CHART

A. Set up the tubes as indicated in the first column below (approx. 12 × 75 glass or polyproyplene tubes) and add reagents in the order indicated.

| TUBE | ADD[1] Folate Standard or Patient Sample | ADD[2] Working Tracer Solution | HEAT 15 min. | COOL | ADD[3] Binding Protein Working Solution | INCUBATION 30 min. | ADD[4] Adsorbent Tablets | |
|---|---|---|---|---|---|---|---|---|
| Total Counts Tube | — | 1.0 ml | — | — | — | — | — | Set Aside |
| Blank | 100 ul P-Zero Std. | 1.0 ml | | | 1.0 ml Dist. H$_2$O | | 1 tablet | |
| Zero ng/ml | 100 ul P-Zero Std. | 1.0 ml | Mix | Cool | 1.0 ml | Incubate | 1 tablet | Proceed |
| 1.0 ng/ml | 100 ul P-1.0 Std. | 1.0 ml | gently. | at | 1.0 ml | at | 1 tablet | to |
| 2.5 ng/ml | 100 ul P-2.5 Std. | 1.0 ml | Cap | room | 1.0 ml | room | 1 tablet | steps |
| 5.0 ng/ml | 100 ul P-5.0 Std. | 1.0 ml | or | tem- | 1.0 ml | tempera- | 1 tablet | below. |
| 10.0 ng/ml | 100 ul P-10.0 Std. | 1.0 ml | cover | pera- | 1.0 ml | ture. | 1 tablet | |
| 20.0 ng/ml | 100 ul P-20.0 Std. | 1.0 ml | tubes | ture. | 1.0 ml | | 1 tablet | |
| Patient Sample | 100 ul Patient Sample | 1.0 ml | loosely. | | 1.0 ml | | 1 tablet | |

B. Allow to stand about 5 minutes. Vortex each tube about 10 seconds. Allow to stand about 5 minutes.
C. Centrifuge 10 minutes at 2000–3000 RPM. Decant into counting vials.
D. Count supernates and total counts tube.

[1]PGA (pteroylglutamic acid) was spiked to folate free serum (or serum protein base) at 0, 1, 2.5, 10, 20 ng/cc level.
[2]About 100,000 cpm of iodinated tyramine derivative of PGA in 1 cc, 0.05 M borate, 0.2% (W/V) dithiothreitol, 0.85% (W/V) NaCl buffer, pH 9.4.
[3]About 40 ug to 70 ug of -lactoglobulin in 1 cc 0.002% merthiolate, 0.1% HSA in H$_2$O.
[4]Bio-Rex 5 tablets prepared as described below.

The following steps more specifically describe the use of the above flow sheet:

1. Label two 12 × 75 mm reaction tubes for the blank, two for each standard including Zero, and two for each sample.
2. To the blank tubes add 100 ul P-Zero standard. To the standard tubes add 100 ul of the appropriate standard- P-Zero, P-1.0, P-2.5, P-5.0, P-10.0 and P-20.0. Add 100 ul of each patient sample to the appropriate patient tubes.
3. To all tubes add 1.0 ml of Working Tracer (Note 2, Flow Chart) Solution. Prepare immediately prior to the assay. Mix all tubes gently.
4. Prepare a total counts tube by adding 1.0 ml Working Tracer Solution to a counting vial. Set aside until Step 11.
5. Place the tube rack containing all of the tubes in a boiling water bath for 15 minutes. Cap or cover tubes loosely. Cool to room temperature by placing in a cold water bath.
6. To the blank add 1.0 ml of distilled water. To all tubes except the blank add 1.0 ml of Folate Binding Protein Working Solution (Note 3, Flow Chart) Mix all tubes well.
7. Incubate at room temperature for 30 minutes.
8. At the end of the incubation period, add one Adsorbent Tablet to each tube, allow to stand about 5 minutes. Vortex each tube for approximately 10 seconds. Allow to stand about 5 minutes.
9. Centrifuge all tubes about 10 minutes at about 2000–3000 RPM to pack the adsorbent.
10. Decant the supernatants into appropriately labelled counting vials.
11. Count each supernatant and/or pellet and the total counts tube. Record the counts.

The adsorbent tablet listed in the above flow chart may be made by the following procedure.

Water is removed from the selected resin such as BIO-REX 5, 200–400 wet mesh resin, using a solvent such as methanol and acetone. The resin is dried and reduced to powder form. A suitable amount of tableting agent which will provide an adequate physical integrity of the resin tablet during normal handling but which will break up easily in the aqueous competitive binding solution is blended to form a homogeneous mixture with the resin. A preferred bulking agent is microcrystalline cellulose, such as the material known by the Trademark AVICEL. It has been found that a weight ratio of resin to microcrystalline cellulose of about 1:2 provides tablets having the proper physical properties. However, other ratios can be used. The homogeneous blend of the microcrystalline cellulose is then compressed into tablets by any suitable techniques. Conventional tableting machines can be used for this purpose. Tablet size is such as to provide about 3–140 mg of resin, preferably about 8–67 mg of resin with the balance being microcrystalline cellulose. Such tablets are convenient for use with a serum sample size of 0.1 ml. Suitable lubricants such as stearic acid may be added in the proper amounts.

Utilizing the above assay procedure curves were developed from standard samples. The same procedure but using the charcoal tablet described in U.S. Pat. No. 4,028,465 was run. The results are shown in FIG. 1. For further comparison the same assay procedure was run but with the bound from free separation executed with a tablet formed from strong base anion exchange resin commercially known as Bio-Rad AG1X2 available from Bio-Rad Laboratories, Inc. Richmond, California. The results are shown in FIG. 1.

The improvements in nonspecific binding were determined from the above serum folate assay procedures in which the bound-free separation was executed variously with the prior art charcoal tablet, present intermediate anion exchange resin and the strong base anion exchange resin. Pertinent data obtained from these experiments is shown in the following Table. Attention is invited to the results with respect to nonspecific binding. These results were obtained on procedures in which the tracers were about two weeks old. As the tracer ages through its recommended shelf life of about 60 days, the nonspecific binding obtained with the present improved assay continues to improve relative to the previously used charcoal.

TABLE

| Control Sera | Results in ng/ml with Charcoal Separation | Results in ng/ml with Bio-Rex 5 Resin Separation | Results in ng/ml with Ag 1 × 2 Resin Separation | Values Listed by Manufacturer |
| --- | --- | --- | --- | --- |
| Lederle Ria Lot 2945-432 | 11.0, 10.0 | 12.5, 14.0 | 13.5, 18.0* | 12.8 ± 2.6 |
| Ortho Ria Lot 4P504 | 2.0, 2.0 | 2.0, 2.2 | 2.3, 2.3 | 1.8 ± 0.4 |
| Ortho Ria Lot 5P405 | 8.6, 8.2 | 9.0, 9.1 | 9.1, 9.1 | 9.6 ± 1.4 |
| Non-Specific Binding (blank) | 10.6% | 8.3% | 26.7% | |
| Trace Binding | 65.5% | 62.2% | 51.0% | |

We claim:

1. In a competitive binding assay for serum folate including the step of separating unbound serum folate from serum folate bound by a folate-selective protein, the improvement comprising separating unbound serum folate by removal with an anion exchange resin.

2. The improved competitive binding assay in accordance with claim 1, wherein said anion exchange resin is an intermediate base anion exchange resin.

3. The improved competitive binding assay in accordance with claim 2, wherein said anion exchange resin has an aliphatic lattice.

4. The improved competitive binding assay in accordance with claim 1, wherein said anion exchange resin has an aromatic lattice.

5. The improved competitive binding assay in accordance with claim 3, wherein said anion exchange resin comprises tertiary and quarternary amines on a polyalkyleneamine lattice.

6. The improved competitive binding assay in accordance with claim 5, wherein the active groups in the resin include $R - N^- (CH_3)_2 Cl^+$ and $R \times N^- (CH_3)_2 (C_2H_4OH)Cl^-$, and R = polyalkyleneamine lattice.

7. An assay for serum folate comprising: providing a serum sample solution, treating said solution to free serum folate from serum folate binding proteins, inactivating the latter, competitively binding a portion of said serum folate with a folate-selective protein whereby said solution contains bound and free serum folate, adding about 3-140 mg for each 0.1 ml in the test solution of intermediate base anion exchange resin in dry solid form to said solution to adsorb free serum folate, and separating said anion exchange resin from said solution.

8. The assay in accordance with claim 7, wherein said anion exchange resin is in a compressed tablet form when added to said solution.

9. The assay in accordance with claim 7, wherein said resin is added to constitute about 3-140 mg for each 0.1 ml of serum in a test solution.

10. The assay in accordance with claim 7, wherein said resin is added to constitute about 8-67 mg for each 0.1 ml of serum in a test solution.

11. The assay in accordance with claim 7, wherein said anion exchange resin is about 50-400 wet mesh.

12. The assay in accordance with claim 11, wherein said anion exchange resin is about 200-400 wet mesh.

* * * * *